United States Patent [19]

Muggli

[11] 4,169,708
[45] Oct. 2, 1979

[54] METHOD AND APPARATUS FOR GAS ANALYSIS

[76] Inventor: Robert Z. Muggli, 17938 Homewood Ave., Homewood, Ill. 60430

[21] Appl. No.: 893,576

[22] Filed: Apr. 5, 1978

Related U.S. Application Data

[63] Continuation-in-part of Ser. No. 803,132, Jun. 3, 1977, abandoned.

[51] Int. Cl.² .................. G01N 27/16; G01N 27/18
[52] U.S. Cl. ................................... 23/232 E; 422/93; 422/97
[58] Field of Search ............ 23/232 E, 232 R, 254 E, 23/254 R, 255 E, 255 R; 422/96, 97, 93

[56] References Cited

U.S. PATENT DOCUMENTS

| | | | |
|---|---|---|---|
| 3,088,809 | 5/1963 | Boatman | 23/254 X |
| 3,488,155 | 1/1970 | Ayers | 23/232 R |
| 3,567,394 | 3/1971 | Betz | 23/232 E |
| 3,752,652 | 8/1973 | Vleesschauwer | 23/232 E |
| 3,791,936 | 2/1974 | Pebler et al. | 23/232 R |

Primary Examiner—R. E. Serwin

[57] ABSTRACT

A method and apparatus for determination of oxygen or hydrogen levels in a gas sample. In accordance with the method, a flowing stream of a gas sample containing a minor amount of diluent gas, oxygen and/or hydrogen is provided. A predetermined amount of a gaseous fuel is combined with the flowing stream of the gas sample to provide a reactive mixture. The reactive mixture is passed over a first sensing element and over a second sensing element. Prior to passing the flowing stream of the gas sample over the second sensing element, the stream is passed over a catalyst to cause reaction of oxygen and/or hydrogen with the fuel to produce water and heat. This causes a temperature and a moisture differential to exist between the first sensing element and the second sensing element. The difference in the moisture level or the temperature differential is converted to an electric signal. The electric signal produced is compared with a reference standard whereby the level of the oxygen and/or hydrogen is determined.

11 Claims, 3 Drawing Figures

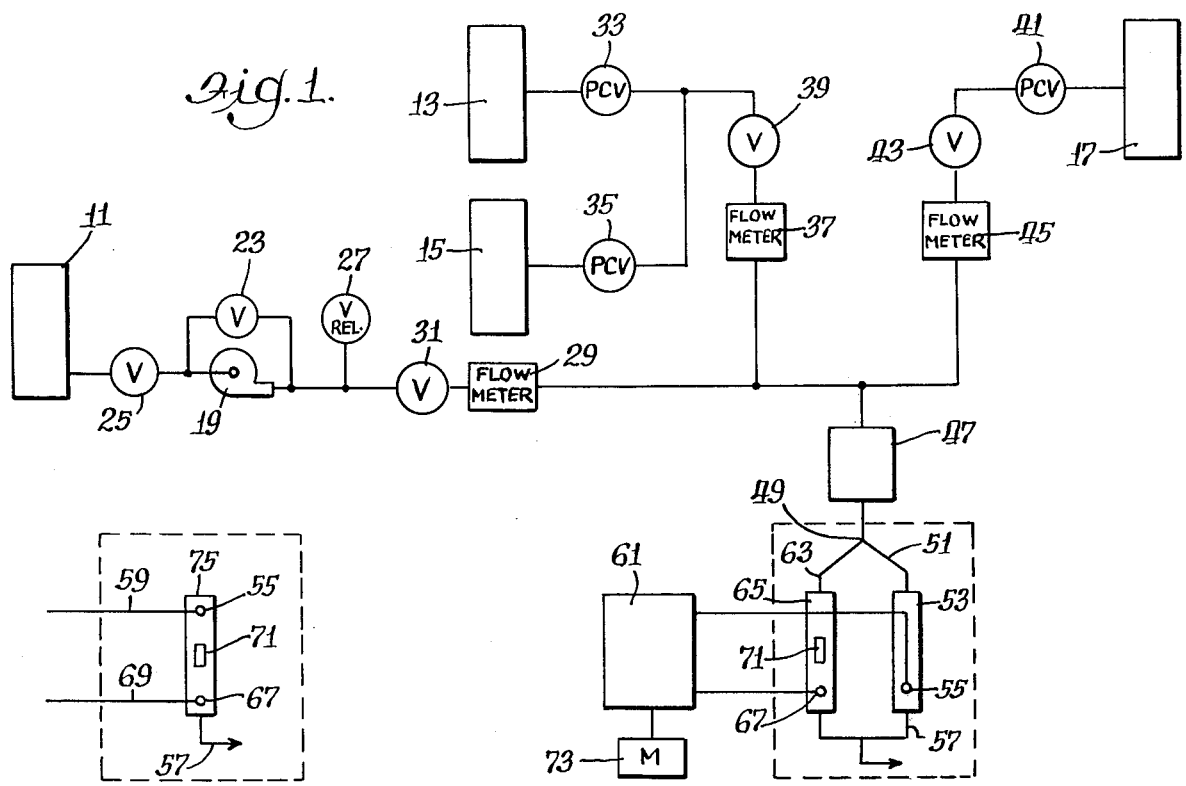
Fig. 1.
Fig. 2.
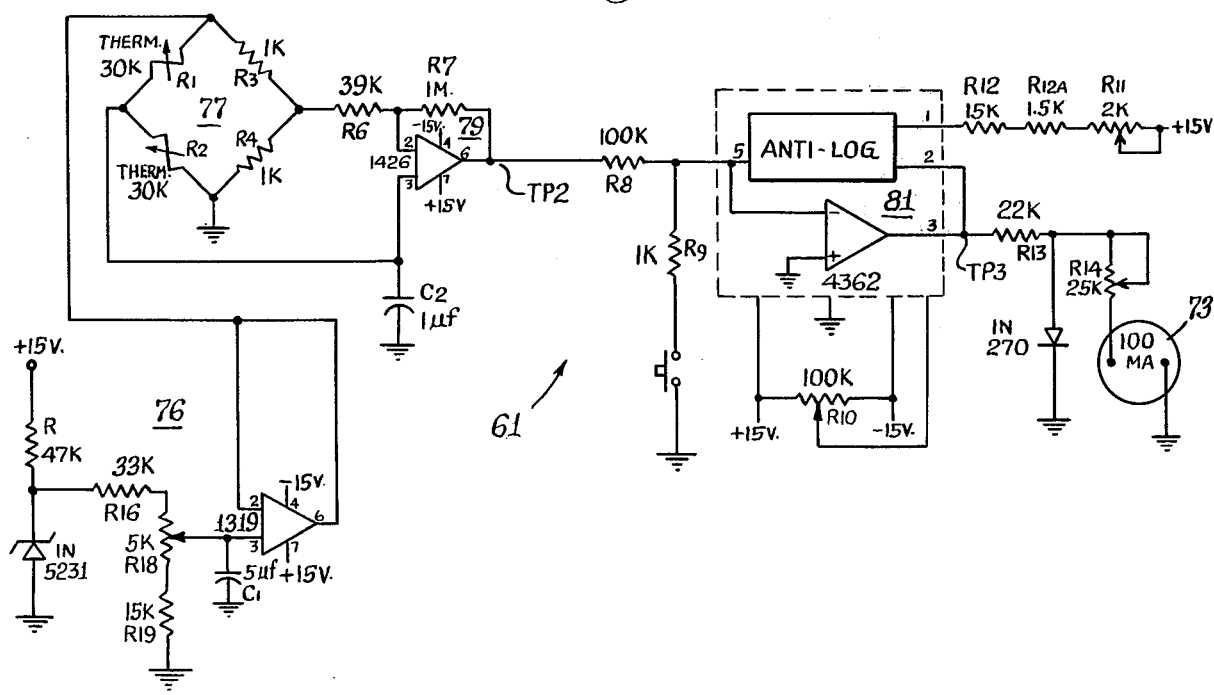
Fig. 3.

METHOD AND APPARATUS FOR GAS ANALYSIS

The present application is a Continuation-In-Part of Application Ser. No. 803,132, filed June 3, 1977, and now abandoned.

The present invention is directed generally to a method and apparatus for determination of oxygen or hydrogen levels in a gas sample, particularly a gas sample containing minor amounts of oxygen and/or hydrogen. More particularly, the present invention is directed to a method and apparatus for determination of oxygen and hydrogen levels in a gas sample by reacting the oxygen or hydrogen with a fuel at ambient temperature and measuring the moisture or thermal energy created by the reaction.

Various methods and apparatus are known for determining oxygen and hydrogen levels in gas samples. It is also known to use temperature differentials between burned and unburned gas samples to measure combustible gas levels in a gas sample. However, such known devices have operated at high temperatures and are not selective as to oxygen or hydrogen. Magnetic and membrane type devices are known for specific determination of oxygen and hydrogen. However, such magnetic and membrane types of analytic apparatus are not sufficiently sensitive to measure low levels of oxygen or hydrogen below about 2 percent of the total volume of the gas sample.

It would be desirable to provide analytic apparatus and a method for using such apparatus for determination of oxygen and hydrogen in a gas sample which is operable at ambient temperatures. It would also be desirable to provide apparatus which is specific to determination of either oxygen or hydrogen when oxygen and/or hydrogen is present in a gas sample at a low level of less than about 2 percent of the total volume of the gas sample.

Accordingly, it is a principal object of the present invention to provide apparatus and a method which can be used to determine the level of either oxygen or hydrogen in a gas sample.

It is another object of the present invention to provide a method and apparatus for the determination of low levels of oxygen or hydrogen in a gas sample.

These and other objects of the invention will become more apparent from the following detailed description and the accompanying drawings wherein:

FIG. 1 is a schematic diagram of one embodiment of apparatus in accordance with the invention;

FIG. 2 is a schematic diagram of a further embodiment of the portion of the apparatus of FIG. 1 shown in the dashed outline section of FIG. 1; and FIG. 3 is an electrical schematic diagram of the signal comparator of the present invention.

Generally, the present invention is directed to a method and apparatus for determination of oxygen or hydrogen levels in a gas sample containing minor amounts of oxygen or hydrogen. In accordance with the method, a flowing stream of a gas sample containing a minor amount of oxygen and/or hydrogen is provided. The pressure of the flowing stream is regulated and the flow rate of the flowing stream is measured. A predetermined amount of a gaseous fuel is combined with the flowing stream of the gas sample to provide a reactive mixture. The reactive mixture is passed over a first sensing element and thereafter over a second sensing element. The first and second sensing elements are selected from electrothermic transducers and low level moisture detectors. Prior to passing the flowing stream of the gas sample over the second sensing element the stream is passed over a catalyst to cause reaction of the oxygen and/or hydrogen with the fuel to produce water and heat. This also causes a temperature differential to exist between the first sensing element and the second sensing element. The difference in moisture level before and after the catalytic reaction can be detected and converted to an electric property when the first and second sensing elements are moisture detectors. The temperature differential can be converted to an electric signal when the first and second sensing elements are electrothermic transducers. The electric signal produced by the first and second sensing elements is used to activate a meter and is compared with a reference standard whereby the level of the oxygen or hydrogen is determined.

As used herein, the term "electrothermic transducer" refers to those devices which have a variable electric parameter which is a function of temperature. Examples of suitable electrothermic transducers are thermistors (solid state resistors where the resistance is a function of temperature) and thermocouples (two joined dissimilar metallic conductors capable of generating an electromotive force which varies as a function of the temperature of the junction).

Referring now to the drawings, the apparatus and method of the invention will be described in further detail. A preferred embodiment of the apparatus is shown in FIG. 1. As set forth in FIG. 1, the apparatus includes a gas sample container 11, gaseous fuel containers 13 and 15 and a calibrating gas container 17.

The sample gas may sometimes be removed from a low pressure source and a pump 19 is provided to draw the sample gas into the apparatus. If the sample gas is at high pressure, the pump 19 may be bypassed by bypass line 21 which is controlled by shut off valve 23. Shut off valve 25 is provided to isolate the sample gas from the system. The pressure of the sample gas is regulated by relief valve 27 and flow meter 29. The flow rate through flow meter 29 is regulated by valve 31.

The fuel gas and calibrating gas are obtained from pressurized cannisters and no pump is required to draw these gases into the system. Fuel gas from cylinders 13 and 15 is regulated by pressure control valves 33 and 35 and by flow meter 37. The rate of flow through flow meter 37 is regulated by valve 39. The calibrating gas is admitted to the system through pressure control valve 41, valve 43, and flow meter 45.

In operation, either the sample gas or the calibrating gas is combined with a stoichiometric excess of fuel gas in mixing chamber 47. The mixture of gases in the mixing chamber 47 is tempered in temperature by passing ambient air having a temperature not in excess of 30° C. over the mixing chamber 47. The mixture of gas exits from mixing chamber 47 and is divided into two equal streams at the Y fitting 49.

One stream is led through conduit 51 into chamber 53 which is provided with a first sensing element 55. The output from the first sensing element 55 is fed through line 59 to the electric comparator 61. The schematic for a suitable electric comparator 61 is shown in FIG. 3 utilizing thermistors as an electrothermic transducer sensing element and will be described more fully hereinafter. The gas mixture after passing over the first sensing element 55 is exhausted to the atmosphere through conduit 57.

The second part of the gas mixture is routed through conduit 63 to a second chamber 65 and is passed over a second sensing element 67. The output from the second sensing element 67 is fed by lead 69 to electric comparator 61. The gas mixture after passing over the second sensing element 67 is exhausted to the atmosphere through conduit 57.

Prior to reaching the second sensing element 67 the gas mixture is passed over catalyst 71. The catalyst 71 is preferably a molded cylinder of alumina (aluminum oxide) with platinum or palladium deposited on the surface. The platinum or palladium is present at a level of from about 0.2 to about 2 percent by weight of the total catalyst cylinder weight and the total catalyst cylinder weight is from about 0.03 to about 0.08 grams.

The level of catalyst and rate of flow of the calibration and sample gases are selected so that only a partial reaction of the calibration and sample gas is attained. In this connection it is important to prevent the temperature of the catalyst 71 from exceeding about 50° C. At temperatures above about 50° C. other components of the sample gas, such as hydrocarbons, begin to react and the apparatus of the invention loses its specificity for hydrogen or oxygen. For example, complete reaction of only 100 ppm of oxygen or 200 ppm of hydrogen would cause a temperature increase of 25° C. The apparatus of the present invention is designed so that a partial reaction, in situ cooling or the level of diluent gas is regulated so that 100 ppm of oxygen causes only a temperature increase of about 0.17° C.

Catalyst 71 causes some of the oxygen or hydrogen present in the gas mixture to react with the stoichiometric excess of fuel gas. This causes the moisture level and temperature of the gas stream to increase as compared to the moisture level and temperature of the first gas stream. The difference in electrical properties between the two sensing elements 55 and 67 in the two gas streams is detected by the electrical comparator 61 and is converted into a voltage which is read by meter 73.

In another embodiment of the invention shown in FIG. 2, the mixture of gases exiting from mixing chamber 47 is led directly to a chamber 75 containing, in sequence, the first sensing element 55, the catalyst 71 and the second sensing element 67. The moisture level or temperature of the gas mixture before and after being reacted by catalyst 71 is detected by the difference in electric properties between the two sensing elements 55 and 67. and is fed to electric comparator 61 by leads 59 and 69 as previously described.

An electric comparator suitable for reading the minute voltage, current or resistance differentials created by the use of first and second electrothermic transducers as the sensing element is shown in FIG. 3, wherein the electrothermic transducers are thermistors. The comparator includes a regulated bridge power supply circuit 76, a Wheatstone bridge circuit 77, amplifier circuit 79 and log compression circuit 81. The valves shown for various resistors, capacitors, diodes, amplifiers, and potentiometers are representative of suitable components for an electric comparative circuit adapted for use to read the minute resistance changes which occur between two 30 K thermistors which serve as the first sensing element and second sensing element. The diodes are manufactured by RCA and the amplifiers are manufactured by Teledyne Philbrick. A power supply switch (not shown) is used to turn the fifteen volt power supply on and off and to serve as an on and off switch for the comparator circuit.

The electric comparator circuit is adjusted as follows: The power supply switch is turned on to energize the circuits. Valves 25, 39 and 43 are closed so that no sample gas, fuel gas, or calibration gas is introduced to the system. After a 2 to 3 minute warm up, a high impedance volt meter is connected across ground and test point 1 (TP1 in FIG. 3). The power supply voltage for the Wheatstone bridge is adjusted to 1.5 V D C with trimpot R 18. The zero adjust (R4) and calibration adjust (R14) are then adjusted to place the needle of meter 73 near the scale midpoint. The logger offset voltage is adjusted with switch S1 and trimpot R10. Switch S1 is momentarily pressed and R10 is adjusted if meter movement is observed. Adjustments are continued until no meter movement is observed when S1 is depressed and released.

The volmeter is then connected across ground and test point 2 (TP2 in FIG. 3). The zero adjust (R4) on the front panel is adjusted so that the voltage at TP2 is 0.1 for a bridge output of 5.0 m volts or 1.0 volts for a bridge output of 50.0 m volts. Then the voltage at test point 3 (TP3 in FIG. 3) is adjusted with trimpot R11 to provide a voltage of −2.0 V if TP2 is set at 0.1 V or −4.0 V if TP2 is set at 1.0 V.

The zero adjust (R4) is turned until the needle on meter 73 drops to less than 10 on the meter dial. The meter dial is scaled from 10 to 10,000 to indicate direct reading of the gas sample analysis in PPM. Calibration gas valve 43 and fuel gas valve 39 are then opened. If the gas to be analyzed for is oxygen, fuel cylinder 13 containing hydrogen is activated by adjusting PCV valve 33 to provide a pressure of 8 to 10 psig. The fuel flow meter is adjusted with valve 39 for a flow rate of about 0.02 cubic feet per hour. Pressure control valve 41 for the calibration gas flow is adjusted to provide a pressure of 5 to 6 psig and valve 43 is adjusted to provide a flow rate of 2 cubic feet per hour. The calibration gas and fuel gas are then passed to mixing chamber 47 and through chambers 53 and 65.

The calibration gas has a known level of free oxygen, preferably about 500 PPM so that the needle on meter 73 can be adjusted to its midpoint. The needle on the meter 73 is then adjusted by means of trimpot R14 for the correct reading on the meter scale.

The calibration gas supply is then turned off by means of valve 43 and a low pressure sample gas supply is activated by opening valve 25 and starting pump 19. Relief valve 27 is adjusted to provide a pressure of about 3 psig and valve 31 is adjusted to provide a flow rate of 2 cubic feet per hour. The fuel gas is continued to be supplied to the system at a pressure of 8 to 10 psig at a flow rate of 0.02 cubic feet per hour. The mixture of sample gas and fuel gas is transferred through chambers 53 and 65 and the level of oxygen in the sample gas is read directly on the scale of meter 73 in PPM. Other pressures and flow rates within the range of from about 0.5 to about 10 psig and from about 0.5 to about 20 cubic feet per minute are suitable so long as the flow rate of the sample gas is the same as flow rate of calibration gas used to set the meter.

If the gas to be analyzed for in the sample gas is hydrogen, gaseous fuel from container 15, containing oxygen, is supplied to the system and gaseous fuel container 13 is isolated from the system. For oxygen analysis, fuel container 15 is isolated and fuel container 13, containing hydrogen, is activated.

The apparatus and method of the present invention are suitable for the analysis of low levels of oxygen and hydrogen which are present as a diluent in a gas sample. In this connection, if oxygen or hydrogen is present at a level above about 2 percent by volume the amount of heat generated by the reaction with the fuel gas in the presence of the catalyst is too great and a catalyst temperature above 50° C. is attained resulting in reaction of other components in the gas sample, such as hydrocarbons, and the specificity of the apparatus and method for oxygen and hydrogen is lost. For this same reason, it is important in the operation of the apparatus that the catalyst should be maintained at a temperature below about 50° C. It should be understood, however, that high levels of oxygen or hydrogen can be measured by the apparatus of the invention. This is accomplished by mixing the high level gas (having oxygen or hydrogen present at a level above about 2 percent by volume) with a measured ratio of gas free oxygen or hydrogen to provide a low level sample. The low level sample is then analyzed for oxygen or hydrogen with the apparatus of the invention.

The accuracy of measurement of low levels of oxygen and hydrogen in the gas sample with the apparatus of the invention is dependent upon the measurement of extremely small moisture or temperature differences caused by the partial reaction. For example, 50 ppm of oxygen results in a temperature increase of about 0.8° C. and a moisture increase of about 10 ppm. If the reaction were complete, 50 ppm of oxygen would cause a temperature increase of 12.2° C. For this reason, it is necessary, when using electrothermic transducers as the sensing element, that the base temperature of both the first and second electrothermic transducer be maintained at the same value between the time of calibration and the time of making an analysis of a gas sample. This is readily accomplished by drawing a stream of ambient air past first and second chambers 53 and 65 or past chamber 75. The absolute ambient temperature is not critical so long as no substantial variation occurs between the time of calibration and the time of analysis and so long as the temperature after the reaction is below about 50° C. To prevent heat buildup in the reaction chamber containing the catalyst it is preferred that the reaction chamber be constructed from a material with good heat dissipation properties, such as thin-walled glass or quartz. In the embodiment utilizing two chambers it is preferred that the chambers be isolated from each other by means of a heat barrier.

Any suitable moisture detector can be used. Suitable moisture detectors are manufactured by Veekay, Ltd. of Concord, Calif., and Panametrics, Inc. of Waltham, Mass., and these moisture detectors are capable of making direct measurement of the partial pressure of water in both gas and liquid systems. This is achieved through the use of an aluminum oxide sensing element which is mounted directly in the gas stream. The sensor consists of an anodized aluminum strip having a porous aluminum oxide layer. A thin layer of gold is deposited over the oxide surface. This structure of two conductors separated by a dielectric behaves essentially as a capacitor. When the sensor is placed in water containing environment, water molecules absorb on the surface of the aluminum oxide changing its dielectric properties. The concentration of absorbed water is directly proportional to the partial pressure of water vapor. By determining the impedance, a measure of the water vapor pressure in equilibrium with the sensor is made. The signal from the moisture detectors can be either as voltage or current. The Model 3000 Hygrometer manufatured by Panametrics, Inc. is capable of detecting dew points in the range of $-100°$ C. to $+60°$ C. corresponding to moisture levels of about 0.01 ppm to 200,000 ppm (20%).

The above description of the apparatus and method of the invention is representative of various parameters which are useful for the method and apparatus of the invention. It should be understood, however, that other values for the various electrical components, mechanical components, flow rates, pressures and arrangement of apparatus can be made without departing from the scope of the invention as defined in the appended claims.

What is claimed is:

1. A method specific for determination of the oxygen or hydrogen level in a gas sample comprising providing a flowing stream of a gas sample containing a diluent gas selected from one of the group consisting of oxygen and hydrogn, mixing a stoichiometric excess of a gaseous fuel with said stream to provide a reactive mixture, passing said reactive mixture over a catalyst in a reaction chamber whereby said diluent gas is caused to at least partially react with said fuel to produce water and heat, limiting said heat generated by said reaction by means of a method selected from the group consisting of in situ cooling, control of said diluent gas level, partial reaction of said diluent gas and combinations of said methods to limit temperture increase in said catalyst to less than 50° C. so as to prevent reaction of gases other than said diluent gas, passing said reactive mixture over a first sensing element prior to causing said catalytic reaction, passing said reacted mixture over a second sensing element after causing said catalytic reaction, sensing the difference caused by said catalytic reaction in a physical parameter selected from one of the group consisting of moisture and temperature, generating an electric signal by said difference sensing and comparing said electrica signal with the electric signal caused by the difference of a reference standard whereby the level of said diluent gas may be determined.

2. A method in accordance with claim 1 wherein said sensing elements are selected from the group consisting of moisture detectors and electrothermic transducers.

3. A method in accordance with claim 1 wherein the level of said diluent gas in said gas sample is in the range of from about 0.001 ppm to about 20,000 ppm.

4. A method in accordance with claim 2 wherein said sensing element is an electrothermic transducer and wherein said dilutent gas is present in said gas sample at a level of less than about 2 percent by volume.

5. A method in accordance with claim 1 wherein said diluent gas is oxygen.

6. A method in accordance with claim 1 wherein said diluent gas is hydrogen.

7. A method in accordance with claim 5 wherein said fuel gas is hydrogen.

8. A method in accordance with claim 6 wherein said fuel gas is oxygen.

9. A method in accordance with claim 1 wherein said partial reaction of said diluent is insufficient to increase the temperature of said catalyst in said chamber above about 50° C.

10. A method in accordance with claim 1 wherein in situ cooling is sufficient to prevent the increase of the temperature of said catalyst in said reaction chamber above about 50° C.

11. A method in accordance with claim 1 wherein diluent gas level is controlled so that said temperature increase of the said catalyst in reaction chamber is limited to about 50° C.

* * * * *

UNITED STATES PATENT AND TRADEMARK OFFICE
CERTIFICATE OF CORRECTION

PATENT NO. : 4,169,708
DATED : October 2, 1979
INVENTOR(S) : Robert Z. Muggli

It is certified that error appears in the above-identified patent and that said Letters Patent are hereby corrected as shown below:

Column 3, line 57, "valves" should be --values--
Column 5, line 25, "0.8°C" should be --0.08°C--
Column 6, line 17, "hydrogn" should be --hydrogen--
Column 6, line 25, "temperture" should be --temperature--
Column 6, line 36, "electrica" should be --electric--
Column 6, line 46, "dilutent" should be --diluent--

Signed and Sealed this

Twelfth Day of February 1980

[SEAL]

Attest:

SIDNEY A. DIAMOND

Attesting Officer

Commissioner of Patents and Trademarks